United States Patent [19]

Shank et al.

[11] Patent Number: 5,147,317
[45] Date of Patent: Sep. 15, 1992

[54] LOW FRICTION VARIED RADIOPACITY GUIDEWIRE

[75] Inventors: Peter J. Shank, Burlington; Kenneth W. Horton, Westford, both of Mass.

[73] Assignee: C.R. Bard, Inc., Murray Hill, N.J.

[21] Appl. No.: 532,381

[22] Filed: Jun. 4, 1990

[51] Int. Cl.⁵ ............................................. A61M 5/178
[52] U.S. Cl. ..................................... 604/164; 604/282; 128/657
[58] Field of Search ....................... 128/656, 657, 772; 604/164, 282

[56] References Cited

U.S. PATENT DOCUMENTS

| | | | |
|---|---|---|---|
| 3,789,841 | 2/1974 | Antoshkiw | 128/772 |
| 3,841,308 | 10/1974 | Tate | 128/772 |
| 4,030,503 | 6/1985 | Clark | . |
| 4,538,622 | 9/1985 | Samson et al. | 128/657 |
| 4,545,390 | 10/1985 | Leary | . |
| 4,554,929 | 11/1985 | Samson et al. | 128/657 |
| 4,619,274 | 10/1986 | Morrison | . |
| 4,721,117 | 1/1988 | Mar et al. | 604/164 |
| 4,724,846 | 2/1988 | Evans | . |
| 4,748,986 | 7/1988 | Morrison et al. | 128/657 |
| 4,773,432 | 9/1988 | Rydell | . |
| 4,796,642 | 1/1989 | Harris | . |
| 4,811,743 | 3/1989 | Stevens | 128/657 |
| 4,813,434 | 3/1989 | Buchbinder et al. | 128/657 |
| 4,830,023 | 5/1989 | de Toledo et al. | . |
| 4,832,047 | 5/1989 | Sepetka et al. | 128/657 |
| 4,846,186 | 7/1989 | Box et al. | 604/164 |
| 4,867,173 | 9/1989 | Leoni | 128/772 |
| 4,886,067 | 12/1989 | Palermo | 128/772 |
| 4,921,482 | 5/1990 | Hammerslay et al. | 182/772 |
| 4,922,924 | 5/1990 | Gambale et al. | 128/657 |
| 4,941,473 | 7/1990 | Tenerz et al. | 128/657 |
| 4,953,553 | 9/1990 | Tremulis | 128/772 |
| 4,971,490 | 11/1990 | Hawkins | 128/657 |

Primary Examiner—John J. Wilson
Assistant Examiner—Frank A. LaViola
Attorney, Agent, or Firm—Morgan & Finnegan

[57] ABSTRACT

A guidewire for use in the placement of a catheter includes an elongate flexible core wire and a helical coil wrapped about the core wire. The pitch of the turns of the coil is relatively wide over most of the length of the guidewire with a distal segment having coil turns that are closely adjacent each other. The coil is formed from a radiopaque material. The wide pitch of the coil presented reduced contact area between the guidewire and the catheter, thereby reducing frictional drag between the two. The distal dip defines a relatively dark radiopaque image while the more proximal portions of the guidewire present a less radiopaque relatively gray image. The black/gray fluoroscopic images enable clear determination of the precise position and contour of the guidewire but without obstructing fluoroscopic visualization of radiopaque contrast liquid injected into the body lumen containing the guidewire and catheter.

31 Claims, 2 Drawing Sheets

LOW FRICTION VARIED RADIOPACITY GUIDEWIRE

FIELD OF THE INVENTION

This invention relates to guidewires used to assist in the placement of catheters in body lumens.

BACKGROUND OF THE INVENTION

Guidewires are used in numerous catheterization procedures as an aid to placement of a catheter in a selected site within the human body. The catheter is constructed to perform a particular procedure at that internal site. For example, among the more common uses of guidewires is in the catheterization of blood vessels for purposes of diagnosis or treatment. In a common type of vascular catheterization procedure, the guidewire first is inserted, usually percutaneously, into the patient's vascular system and is manipulated and advanced to the target site. The catheter then is threaded over and advanced along the guidewire, with the guidewire serving to guide the catheter directly to the target site. By way of further example, a number of catheterization procedures are performed with respect to the coronary arteries, including diagnostic catheterization procedures in which an angiographic catheter is advanced through the patient's arteries to the entrance to the coronary arteries. A radiopaque contrast liquid then is injected through the angiographic catheter into the coronary arteries under X ray fluoroscopy, so that the anatomy of the patient s coronary arteries may be observed visually. Once the coronary anatomy has been determined, the physician may perform additional catheterization procedures, including percutaneous transluminal coronary angioplasty (PTCA), in which a balloon catheter or other angioplasty catheter is advanced into the coronary arteries to widen an obstructed portion of the artery.

In a typical PTCA procedure, an angioplasty catheter, which may be in the form of an elongate flexible shaft with an inflatable balloon at its distal end, is advanced from a percutaneous puncture site in the patient s femoral artery through the patient's arteries to and into the coronary arteries. The catheter is guided to the target site of the obstruction by use of a slender guidewire which initially is advanced into and manipulated through the coronary arteries, in advance of the dilatation catheter. Once the distal end of the guidewire is in place within the obstruction, the catheter then is advanced over the guidewire which guides the catheter directly to the obstruction to place its balloon within the obstruction. The balloon then is inflated to dilate the obstructed portion of the artery, thereby enlarging the flow area through the artery.

Guidewires used with PTCA catheters are of special design. Although they are extremely slender, of the order of 0.010"-0.018" diameter, they nevertheless must be capable of transmitting rotation from the proximal end of the guidewire to the distal end in order that the physician may steer the guidewire and manipulate it to the target site in the intended coronary artery. Additionally, the distal end of the guidewire must be very flexible in order that the distal portion of the guidewire can pass through sharply curved, highly tortuous coronary anatomy as well as to provide a soft, floppy distal tip that will not injure the artery or its delicate inner surface.

It is desirable that the physician be able to feel the response of the guidewire as it is manipulated and advanced through the patient's arteries. By having increased sensitivity to its movement, the physician may better control the guidewire. In order to enhance that sensitivity, it is desirable that the guidewire and dilatation catheter through which the guidewire passes, have low frictional resistance without sacrificing the degree to which the guidewire displays other desirable characteristics. It also is among the desirable features of a guidewire that it have sufficient column strength so that it can be pushed without buckling. The guidewire should have sufficient torsional rigidity to transmit torque sufficiently to enable the rotated position of the distal end of the guidewire to be controlled from its proximal end, where the physician grasps the guidewire. These features must be incorporated into a guidewire which also displays a sufficiently high degree of flexibility at its distal end in order to conform safely to sharp bends and tortuous coronary anatomy.

In addition to the foregoing, it also is important that a distal segment of the guidewire is highly radiopaque so that its position can be observed under X-ray fluoroscopy. That enables the physician to observe the location and configuration of the distal end of the guidewire as the guidewire is manipulated and advanced through the patient's arteries. In procedures, such as coronary angioplasty, in which a catheter is advanced through the patient's arteries, it often is the practice to inject radiopaque contrast liquid periodically into the artery so that the shape and path of the artery may be visualized fluoroscopically. With conventional guidewires used in PTCA, the radiopacity of the guidewire coil may be so dense as to visually obstruct part of the artery which the physician may desire to view when the contrast liquid is injected. For use in such instances, it would be desirable for the guidewire to be only partially highly radiopaque, that is, to form a light but visible gray shadow in some portions and a heavy, dark fluoroscopic image on another.

It is among the general objects of the invention to provide a guidewire that satisfies all of the above objectives.

SUMMARY OF THE INVENTION

The guidewire of the present invention includes an elongate flexible core wire that is of uniform diameter over the major portion of its length with a distal portion being of reduced diameter to provide for increased flexibility at the distal end of the guidewire. The core wire is wrapped with a helical coil formed from a smaller diameter wire. The helical coil wire is formed from a relatively highly radiopaque material, such as a platinum alloy. The helical coil, along a proximal segment of the core wire, is wrapped with its coils in close contact with each other to define a maximum diameter, easily gripped handle for manipulation of the proximal end of the guidewire. A significant feature of the present invention is the manner in which guidewire friction is reduced and overall radiopacity is controlled. To that end, the space between adjacent turns of the coil is increased substantially distally of the handle portion so that there is a substantial pitch between adjacent coil turns. The widely pitched turns of the helical coil extend over a major portion of the length of the core wire, including the remainder of the large diameter proximal core portion and over most of the reduced diameter distal portion of the core. The distal end of the helical coil, over a relatively short length of the core wire, has turns that are closely adjacent each other. The helical coil is wrapped closely about the core wire along the length of the core wire except at the distal tip of the helical coil where the turns of the coil increase in diameter to a diameter corresponding to the proximal end of the guidewire and do not contact the core wire. The distal tip of the core wire and the distal end of the helical coil both are attached to a generally hemispherical distal tip weld.

The portion of the guidewire that includes the widely pitched helical coil extends over most of the length of the guidewire. When the guidewire is disposed within the lumen of the catheter, the helical coil contacts and bears against the inner surface of the catheter lumen. Because the turns of the coil are widely spaced along most of the length of the guidewire, the amount of contact between the outermost periphery of the guidewire and the inner surface of the catheter lumen is maintained at a minimum. The substantially reduced contact area between the guidewire and the inner surface of the catheter lumen results in less frictional drag as the guidewire and catheter are moved relative to each other. Consequently, the physician will have increased sensitivity and responsiveness when manipulating one of the catheter or guidewire with respect to each other.

The relatively short closely pitched coils at the distal end will present a more radiopaque mass to the X-rays during fluoroscopic observation of the position of the guidewire. The portion of the coil just proximal of the highly radiopaque distal segment defines a coil pitch transition region in a distal direction from the widely pitched portion to the closely pitched distal tip. The coil transition region will present a lighter but noticeable, relatively gray, radiopaque image on the fluoroscope thereby providing the physician with an indication of the configuration of the guidewire and coronary anatomy for that portion of the wire but without obstructing the fluoroscopic image of radiopaque contrast liquid that may be injected into the blood vessel. The coil transition region also provides the guidewire with a gradual change in flexibility from a more stiff proximal portion to a more flexible distal portion thus also providing a strain relief function to avoid sharp stress riser bends in the core wire. Additionally, the maximum diameter along the proximal portion of the guidewire and the reduced diameter distal portion provides sufficient torsional rigidity and column strength while providing high flexibility at the distal end to facilitate manipulation and advancement of the guidewire while maintaining a low risk of trauma.

It is among the general objects of the invention to provide an improved guidewire construction.

Another object of the invention is to provide a guidewire for us with catheters in which the frictional drag between the guidewire and the catheter is reduced significantly.

Another object of the invention is to provide a guidewire of the type described in which the distal tip is highly radiopaque and a more proximal segment is relatively lightly but noticeably radiopaque.

A further object of the invention is to provide a guidewire of the type described which has sufficient column strength and torsional rigidity to be pushable and steerable yet in which the distal portion of the guidewire is highly flexible.

Another object of the invention is to provide a guidewire of the type described which is adapted for use in percutaneous transluminal angioplasty, including coronary angioplasty.

DESCRIPTION OF THE DRAWINGS

The foregoing and other objects and advantages of the invention will be appreciated more fully from the following further description thereof with reference to the accompanying drawings wherein.

DESCRIPTION OF THE PREFERRED EMBODIMENT

Figure 1:
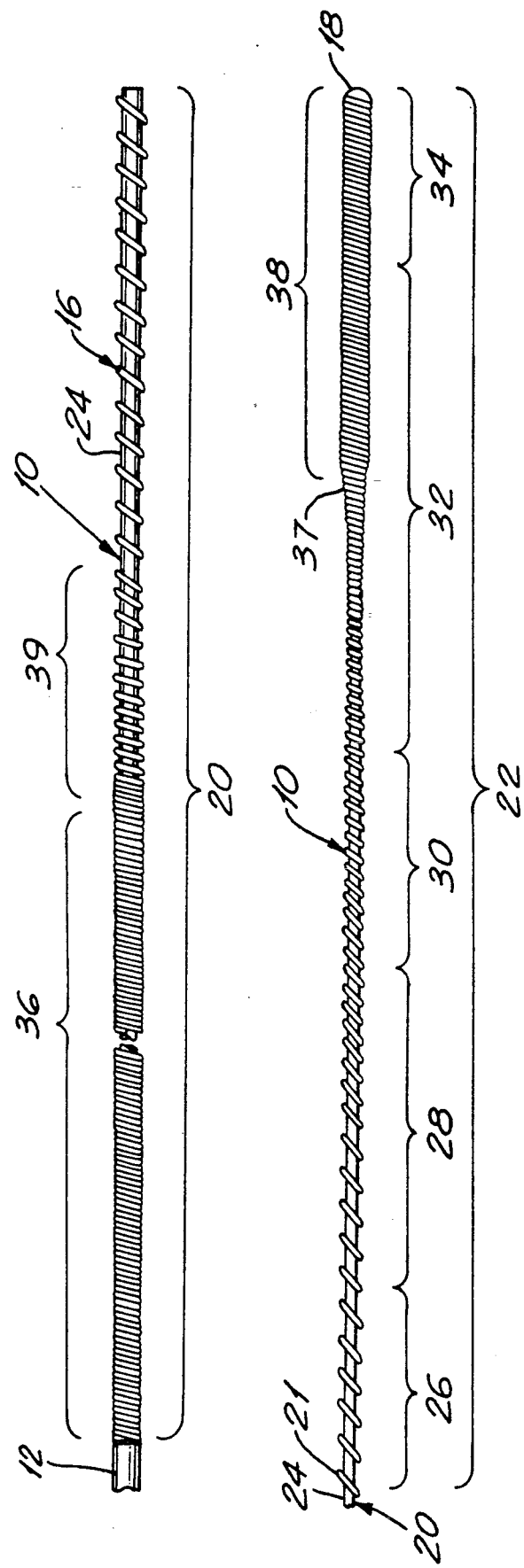
FIG. 1 is a fragmented illustration of the guidewire.

As shown in the drawings, the guidewire may be considered as having a proximal end (to the left in FIG. 1) and a distal end (to the right in FIG. 1). In use, the distal end is inserted into the patient and the proximal end is located exteriorally of the patient where it can be grasped and manipulated by the physician. The guidewire includes an elongate flexible core wire, indicated generally by the reference character 10. The core wire preferably is formed from stainless steel or other suitable flexible, straight, strong material. The core wire 10 extends over substantially the full length of the guidewire. The proximal end of the guidewire may have a tubular extension 12 attached to the proximal end to define a socket 14 or other connector. The socket 14 may be used to receive a guidewire extension (not shown) to facilitate catheter exchanges as described in detail in copending application Ser. No. 206,008 filed Jun. 13, 1988 entitled "Guidewire Extension with Self-Latching Detachable Connector", the disclosure of which is incorporated herein by reference in its entirety. The core wire 10 is wrapped with a helical coil, indicated generally by the reference character 16. The helical coil 16 preferably is formed from highly radiopaque wire, as will be described. The distal tips of the core wire 10 and helical coil 16 are securely attached to a hemispherical tip member 18 which may be formed by a weld or by brazing, soldering or other suitable bonding agent.

The overall length of the guidewire may be varied to suit the particular catheter with which the guidewire is intended to be used and will be longer than the catheter. For example, in a guidewire intended to be used with a PTCA catheter, the catheter may be of the order of 145 cm long and the guidewire may be of the order of 185 cm long. The guidewire may be considered as having a proximal portion 20 that extends from the proximal end of the guidewire to a transition point indicated at 21, and a distal portion 22 that extends distally of the transition point 21. The proximal portion 20 of the guidewire may be considered as including that portion 24 of the core wire 10 that is of uniform maximum diameter and extends from the proximal end to the transition point 21. By way of example, in the illustrative embodiment, the proximal portion 24 of the core wire 10 may be of the order of 140 cm long and may have a diameter of 0.008". The distal portion 22 of the guidewire may be considered as including that portion of the core wire 10 that is of reduced diameter and is more flexible than the proximal portion 20. In the illustrative embodiment, the reduced diameter, more flexible portion of the core wire begins at the transition point 21 and extends toward the distal end of the guidewire. Preferably the diameter of the core wire 10 in the distal portion 22 of the guidewire reduces in diameter in a step taper defined by alternating decreasing tapered and uniform diameter barrel segments, although other tapering configurations may be employed.

In the illustrative embodiment, the guidewire is shown as having a first tapered segment 26 which may be about 6 cm long and which merges into a uniform first distal cylindrical segment 28 of uniform diameter. The first distal cylindrical segment 28 may have a diameter of about 0.006" to 009" and may be approximately 6 to 9 cm long. The first distal segment 28 merges into a second tapering segment 30 that may be about 6 cm long and may reduce in diameter to about 0.004" to 0.006". The second tapering segment 30 in turn merges into a second distal cylindrical segment 32 of uniform diameter which, in turn, merges into a tapering tip segment 34 about 5 cm long. The second distal segment may be approximately 0.004"-0.006" in diameter and about 15 cm in length. The tapering tip segment 34 may be about 5 cm long and may taper to a diameter of the order of about 0.002" which is then flattened as will be described.

The helical coil 16 is wrapped about the core wire 10 over substantially the entire length of the core wire. The helical coil 16 is wrapped directly on the core wire 10, using the core wire as a rotating mandrel in accordance with conventional coil winding techniques as will be apparent to those skilled in the art. The helical coil 10 is formed from wire of the order of 0.002" diameter. The wire of the helical coil 16 is relatively highly radiopaque and may be formed, for example, from an alloy of platinum such as 92% platinum, 8% tungsten or an alloy of 30% gold, 70% platinum.

The pitch of the adjacent turns of the coils varies at different portions along the guidewire, with at least a major portion of the length of the helical coil having adjacent turns spaced form each other by an amount at least equal to the diameter of the wire from which the helical coil is formed. A short proximal segment 36 of the coil is wound in a close pitch in which the turns of the coil lie closely adjacent each other. The proximal segment 36 of the coil may extend over a length of about 25 cm. The proximal segment 36 of the coil is attached securely to the core wire at braze joints 33, 35. The closely wound proximal segment 36 of the coil may serve as an enlarged diameter handle by which the physician may better grasp and manipulate the guidewire. Distally of the proximal segment 36 of the coil 16, the pitch of the adjacent turns of the coil 16 begins to expand progressively (exponentially) in a distal direction. The expansion occurs over a proximal coil pitch transition region 39. The coil pitch expands substantially and may be of the order of 0.75" between turns. The transition region 39 assures a smooth transition in flexibility along the guidewire and may extend over a length of about 10 to 15 cm. The gradual change in pitch through the transition region 39 avoids the development of stress risers in the core wire that might occur with a sharp pitched transition.

The relatively large pitch of the coil is continued distally to the end of the proximal portion 24 of the core wire and continues into the distal portion 22 of the guidewire. The wide pitch of the helical coil continues over the first tapered segment 26 of the core wire. In the illustrative embodiment, the pitch of the coil begins to change about 25 to 30 cm from the distal tip of the guidewire. As illustrated, the pitch begins to change in the region of the juncture of the first tapered segment 26 and first distal segment 28. From that region, the pitch of the coil decreases progressively (preferably exponentially) over a distance of about 10 to 15 cm to a point indicated at 37 where the pitch of the turns of the coil 16 again closes. The region of decreasing pitch, from the juncture of the first tapered segment 26 and first distal segment 28 to the closure point 37 may be considered as a distal coil pitch transition region. The distal pitch transition region serves to provide a smooth progressive change between widely pitched and closely pitched portions of the coil and thereby avoids the development of stress risers which might weaken the core wire upon flexure of the distal end of the guidewire. Additionally, the distal transition region presents a progressively darkening radiopaque image under fluoroscopy, making the transition from a very lightly or almost imperceptibly radiopaque configuration through a relatively gray, moderately opaque portion and to a highly radiopaque portion where the coil pitch approaches and becomes very close.

The foregoing arrangement provides a distal tip segment that is highly radiopaque so that its position can be observed clearly under X-ray fluoroscopy. The more proximal transition region presents a gray, moderately radiopaque segment that provides an indication of the position and configuration of that portion of the artery in which it is contained yet which will not obstruct X-ray fluoroscopic visualization of that portion of the artery when radiopaque contrast liquid is injected into the artery. The turns of the coil lie adjacent each other in a distal portion of the region of the second distal segment 32. The turns of the coil 16 remain in the close pitch configuration to the distal tip of the guidewire, where the distal end of the coil is attached to the tip weld 18.

Figure 2:
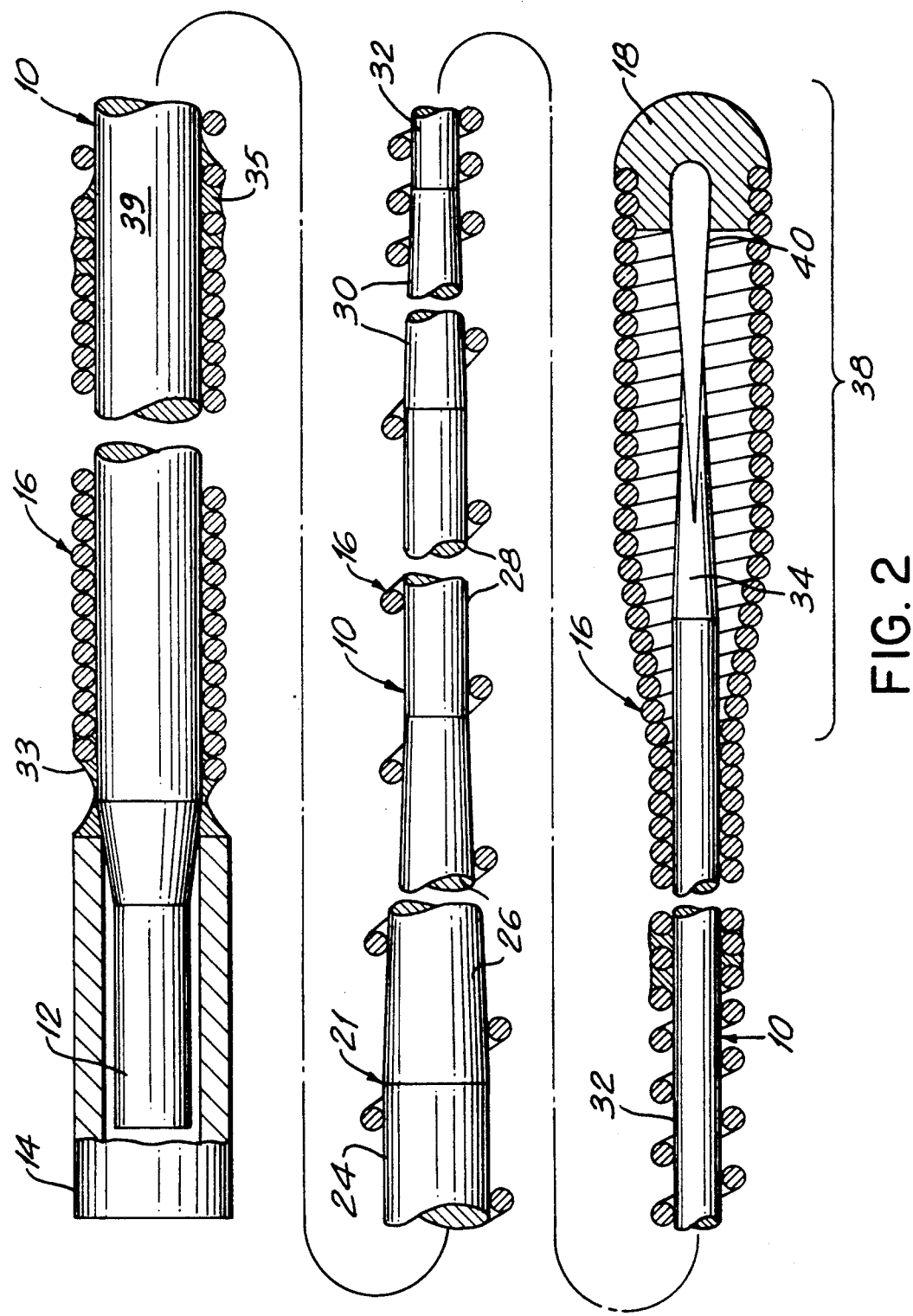
FIG. 2 is a fragmented, sectional, enlarged, illustration of the guidewire.

The helical coil 16 is in contact with and is wound closely about the core wire except for a most distal portion 38 of about four inches in length illustrated in detail in FIG. 2. In that distal most portion, the diameter of the coils increases to a diameter substantially the same as that of the closely pitched coils at the proximal end of the guidewire and continues at that diameter to the tip weld. The distal tip of the core wire preferably is flattened, as by drop flattening, as indicated at 40. The flattened portion 40 may be of the order of 0.001" thick and 0.006" wide. It enables the distal tip of the guidewire to be bent into a curved or J configuration which facilitates selection between coronary artery branches as the guidewire is rotated and manipulated by the physician. It should be noted that the flattened portion 40 is formed in a tapered segment, 34, rather than in a constant diameter cylindrical portion. By forming the flattened tip in a tapered tip, the steerability and torque responsiveness of the guidewire is enhanced. Additionally, such a distal taper would enable a braze joint to be formed at the larger diameter proximal end of the tip taper should that be desired.

The larger diameter coils at the distal tip are free to shift about more readily than with those portions of the coil that are wrapped about the core wire. Thus, the distal portion 38 of the coil provides a flexible floppy atraumatic tip. Additionally, the enlarged diameter of the closely adjacent coils provides a relatively large mass that is sufficiently radiopaque as to be readily observable under fluoroscopy.

Although the guidewire construction described above has substantially reduced surface contact between the guidewire and the inner lumen of the catheter with which the guidewire is used, it may be desirable to further reduce friction between the two. To that end, the guidewire may be coated with a lubricious material such as, for example, a thin coat of Teflon primer (e.g., polytetrafluoroethylene). The primer may be of the order of 0.0004" thick. The Teflon primer is desirable in that it also tends to cause the coil to adhere to the core wire to prevent the helical coil from shifting about along the length of the core wire. Alternately, other coatings may be used, such as a silicone coating available from Dow Corning under the trade designation MDX4.

It should be understood that the dimensions described above in connection with the preferred embodiment are intended to be illustrative and that they may be modified, as desired, to modify the characteristics of the guidewire such as, for example, its flexibility at selected locations and the like.

The foregoing guidewire construction provides a number of advantages. The widely spaced pitch of the adjacent coils along the major portion of the length of the guidewire reduces very substantially the area of contact between the guidewire and the inner surface of the catheter with which the guidewire will be used. Consequently, there will be less resistance to guidewire movement within the catheter lumen. Although this is desirable generally, it is particularly advantageous in a coronary angioplasty setting in which the sensitivity of the physician to the feel of the guidewire is very important when advancing and manipulating the guidewire. Additionally, the guidewire will present an image under fluoroscopy in which the distal segment of the guidewire, where the coils are closely pitched will appear very dark. A more proximal portions, where the coils have an increased pitch will present a reduced, relatively gray appearing radiopaque image. The more proximal portions of the coil having the maximum pitch may be spaced sufficiently to present no substantially discernible radiopaque image. The configuration of a relatively black distal tip and a relatively gray more proximal portion is desirable in that it provides a clear indication of the location of the distal tip of the guidewire in the patient's coronary arteries without completely obstructing the more proximal regions of the artery where the guidewire is located. The fluoroscopically gray portion of the guidewire thus enables the physician to see the contour of the artery without completely obstructing the artery. Additionally, when radiopaque contrast liquid is injected into the coronary artery, the details of the coronary anatomy can be seen through the gray image. Moreover, these advantages are achieved without sacrificing pushability or torsional control while maintaining a soft atraumatic tip.

It should be understood that the foregoing description of the invention is intended merely to be illustrative thereof and that other embodiments, modifications and equivalents may be apparent to those skilled in the art without departing from its spirit.

Having thus described the invention, what I desire to claim and secure by Letters Patent is:

1. A guidewire for use with a catheter comprising:
   an elongate flexible core wire;
   a helical coil formed from a wire having a predetermined diameter, the helical coil being wrapped about the core wire and extending along the length of the core wire, at least a major portion of the length of the helical coil having adjacent turns spaced from each other by an amount at least equal to the diameter of the wire from which the helical coil is formed.

2. A guidewire as defined in claim 1 wherein the distal end of the core wire is of reduced diameter to increase the flexibility of the distal portion of the guidewire.

3. A guidewire as defined in claim 2 wherein the distal portion of the guidewire is tapered.

4. A guidewire as defined in claim 3 wherein said taper comprises a step taper.

5. A guidewire as defined in claim 4 wherein said step taper comprises a series of constant diameter cylindrical sections and alternating tapered sections.

6. A guide wire as defined in claim 5 wherein the most proximal of the constant diameter sections of the core wire extends along a major portion of the length of the guidewire to enhance the torsional rigidity of the guidewire.

7. A guide wire as defined in any of claims 1–6 further comprising:
   a distal segment of the coil having closely spaced adjacent turns.

8. A guide wire as defined in claim 7 wherein said coil is formed from a highly radiopaque material.

9. A guide wire as defined in claim 8 wherein the closely adjacent turns of the coil in the distal segment define a relatively dark radiopaque region under fluoroscopy and where the next adjacent proximal segment having increased pitch turns define a moderately radiopaque segment having a relatively gray image.

10. A guide wire as defined in claim 9 wherein said moderately radiopaque segment is formed by the coils being of progressively decreasing pitch in a distal direction, whereby the opacity of the guidewire may progressively increase along said moderately radiopaque segment.

11. A guide wire as defined in claim 10 wherein the pitch of the coil proximally of said moderately radiopaque segment is such that it present a substantially non-radiopaque image under fluoroscopy.

12. A guide wire as defined in claim 7 further comprising a lubricious coating on the coil.

13. A guide wire as defined in claim 8 further comprising a lubricious coating on the coil.

14. A guide wire as defined in claim 9 further comprising a lubricious coating on the core wire.

15. A guide wire as defined in any of claims 2–6 wherein the outer diameter of the coil reduces in diameter as the core wire reduces in diameter and wherein the coil is in contact with the core wire.

16. A guide wire as defined in claim 15 wherein the diameter of the coil of the distal portion of the guidewire increases and is out of contact with the core wire.

17. A guide wire as defined in claim 16 wherein th end of the core wire is flattened and thin, the distal end of the core wire and the distal end of the coil being attached to a hemispherical tip.

18. A guide wire as defined in claim 17 wherein the end of the core wire is tapered and the flattened portion is formed in the tapered portion.

19. A guide wire as defined in claim 15 wherein the coil is formed from a highly radiopaque material.

20. A guide wire as defined in claim 16 wherein the coil is formed from a highly radiopaque material.

21. A guide wire as defined in any of claims 1–6 further comprising a lubricious coating on the coil.

22. A guidewire as defined in any of claims 1–6 wherein the guidewire is sufficiently torsionally rigid to transmit controllably to the distal end of the guidewire rotation applied to the proximal end.

23. A guidewire as defined in any of claims 1-6 wherein the coil extends along substantially the full length of the core wire.

24. A guidewire for use with a catheter comprising:
an elongate flexible core wire;
a helical coil wrapped about the core wire, the coil having a distal segment in which the adjacent turns of the coil lie closely adjacent to each other and wherein the portion of the coil immediately proximal of the distal segment has turns that are pitched relatively wide;
said coil being formed from a highly radiopaque material whereby the distal segment of the guidewire may define a dark image under fluoroscopy and where the more proximal portion of the guidewire may define a less radiopaque, gray fluoroscopic image.

25. A guidewire as defined in claim 24 wherein a distal portion of the core is of reduced diameter;
the portion of the coil having widely pitched turns extending over most of the proximal portions of the core and part of the reduced diameter portion of the core.

26. A guidewire as defined in claim 1 or 24, the guidewire being of the order of 185 cm in length and having a maximum outer diameter no greater than about 0.018", said maximum diameter extending over the major portion of the length of the guidewire, the distal portion of the guidewire being of reduced outer diameter.

27. A guidewire as defined in claim 26 further comprising:
the core wire having a diameter of approximately 0.008" at its proximal portion, the helical coil being formed from wire having a diameter of the order of 0.002".

28. A method for placing a catheter comprising:
providing a guidewire having an elongate flexible core wire and a helical coil wrapped about the core wire and extending along the length of the core wire, at least a major portion of the length of the helical coil having adjacent turns spaced from each other by an amount at least equal to the diameter of the wire from which the helical coil is formed;
locating the guidewire within a body lumen of the patient; and
advancing the catheter over the guidewire.

29. A method as defined in claim 28 wherein the coil of the guidewire is formed from a highly radiopaque material, the method further comprising injecting radiopaque contrast liquid into the portion of the patient's body lumen that contains the guidewire whereby a radiopaque distal segment of the coil will be clearly apparent under fluoroscopy and where a more proximal portion may be lightly discernible under fluoroscopy thereby to enable the distal and proximal segments of the guidewire to be observed but in which the proximal segment does not obstruct fluoroscopic viewing of injected contrast liquid.

30. A method for placing a catheter comprising:
providing a guidewire having an elongate flexible core wire and a helical coil wrapped about the core wire, the coil having a distal segment in which the adjacent turns of the coil lie closely adjacent to each other and the portion of the coil immediately proximal of the distal segment has turns that are pitched relatively wide;
locating the guidewire within a body lumen of the patient; and
advancing the catheter over the guidewire.

31. A method as defined in claim 30 wherein the coil of the guidewire is formed from a highly radiopaque material, the method further comprising injecting radiopaque contrast liquid into the portion of the patient's body lumen that contains the guidewire whereby a radiopaque distal segment of the coil will be clearly apparent under fluoroscopy and where a more proximal portion may be lightly discernible under fluoroscopy thereby to enable the distal and proximal segments of the guidewire to be observed but in which the proximal segment does not obstruct fluoroscopic viewing of injected contrast liquid.

* * * * *